United States Patent
Roßner et al.

(10) Patent No.: US 7,993,353 B2
(45) Date of Patent: Aug. 9, 2011

(54) MEDICAL TRACKING SYSTEM WITH UNIVERSAL INTERFACE

(75) Inventors: Holger-Claus Roßner, Feldkirchen (DE); Frank Reimold, Ottenhofen (DE); Robert Schmidt, München (DE); Rainer Birkenbach, Aufkirchen (DE)

(73) Assignee: Brainlab AG, Feldkirchen (DE)

( * ) Notice: Subject to any disclaimer, the term of this patent is extended or adjusted under 35 U.S.C. 154(b) by 1904 days.

(21) Appl. No.: 10/447,458

(22) Filed: May 29, 2003

(65) Prior Publication Data

US 2003/0225329 A1 Dec. 4, 2003

Related U.S. Application Data

(60) Provisional application No. 60/385,807, filed on Jun. 4, 2002.

(51) Int. Cl.
*A61B 19/00* (2006.01)
*A61F 2/38* (2006.01)
(52) U.S. Cl. ..................... 606/130; 600/429
(58) Field of Classification Search .............. 606/130; 600/429, 427, 411, 414, 417
See application file for complete search history.

(56) References Cited

U.S. PATENT DOCUMENTS

| | | | |
|---|---|---|---|
| 5,695,501 A * | 12/1997 | Carol et al. | 606/130 |
| 6,223,067 B1 | 4/2001 | Vilsmeier et al. | |
| 6,351,659 B1 | 2/2002 | Vilsmeier | |
| 6,491,699 B1 * | 12/2002 | Henderson et al. | 606/130 |

OTHER PUBLICATIONS

Terry M. Peters, "Image-Guided Surgery: From X-rays to Virtual Reality." Computer Methods in Biomechanics and Biomedical Engineering.

* cited by examiner

*Primary Examiner* — Vy Q Bui
(74) *Attorney, Agent, or Firm* — Renner, Otto, Boisselle & Sklar, LLP

(57) ABSTRACT

An improved marker system, components and method for use with a medical navigation system, wherein the marker system includes interchangeable tracking marker holders and fastener bases for attaching the marker holders to instruments or body parts that are to be tracked during a medical procedure. A reference star (the marker holder and tracking marker(s)) and fastener base are removably attached to one another. This enables different reference stars to be interchangeably attached to a given fastener base, or vice versa, thereby to provide the best combination of reference star and fastener base for a given application. This preferably is accomplished by a standard interface between the fastener base and the holder for the tracking markers, e.g., reflective markers. In addition, surgical instruments may have integrally formed therein the standard interface, thereby eliminating the need for a fastener base.

31 Claims, 1 Drawing Sheet

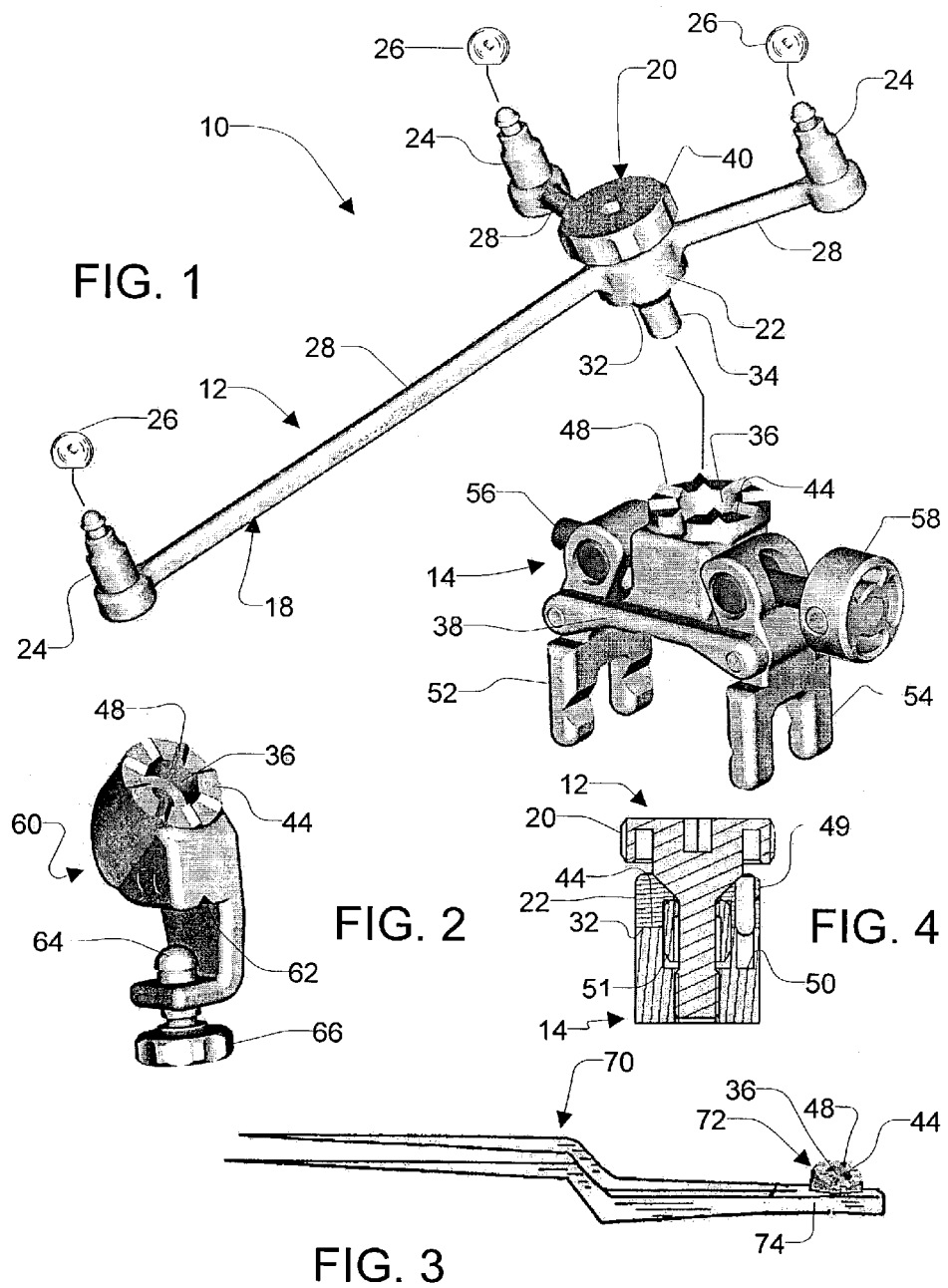

MEDICAL TRACKING SYSTEM WITH UNIVERSAL INTERFACE

This application claims the benefit of U.S. Provisional Application No. 60/385,807, filed Jun. 4, 2002 which is hereby incorporated herein by reference in its entirety.

BACKGROUND OF THE INVENTION

1. Field of the Invention

The invention herein described relates to a marker system for use with a medical navigation system, wherein the marker system includes interchangeable tracking marker holders and bases for attaching the marker holders to instruments that are to be tracked during a medical procedure.

2. Description of the Prior Art

Medical navigation systems, such as image-guided surgery systems, provide medical practitioners, such as surgeons, with navigation information by registering pre-operative images to the physical space of a patient. Most existing systems provide instrument guidance, indicating the position of the instrument in the pre-operative images on a display during the medical procedure. Navigation guidance systems provide increased confidence and precision in the use of medical instruments.

Navigation guidance systems use a computer to which one or more tracking sensors are connected. The tracking sensors track the position of artificial or natural landmarks (herein generically referred to as tracking markers) affixed to the patient and/or instruments, whereby the position of the patient and/or instruments can be determined and registered to pre-operative images of the patient. These tracking markers include active emitters that emit electromagnetic, magnetic or acoustic signals to one or more tracking cameras or devices, and passive reflective markers that reflect light to one or more tracking cameras. The medical instruments with which such tracking markers have been employed include pointers, scalpels, forceps, microscopes, ultrasonic transducers, etc.

Heretofore, adapters have been used to attach replaceable passive reflective markers to surgical instruments. This allowed surgeons to use surgical instruments with which they were more familiar than the specially manufactured surgical instruments that used active tracking markers. The passive reflective markers could be removed for sterilization of the surgical instrument in an autoclave and new reflective markers installed for the next surgical procedure.

The present day adapter typically includes an adapter body including a fastener base and three or more arms that radiate outwardly from the fastener base. The distal ends of the arms have mounts to which respective reflective markers are removably attached. The fastener base includes a clamp for attaching the adapter body to the medical instrument or body part to be tracked by the navigation system. In order to track multiple instruments, adapters having different characteristic arrangements of the reflective markers are provided. Different characteristic arrangements are obtained by varying the length and angular relationships of the adapter arms. Because of the central mounting (or hub) portion and the radiating arms with the reflective markers at the distal ends thereof, the adapters with the reflective markers are often referred to as reference stars.

A well-known navigation system that uses the aforedescribed reference stars is the VectorVision™ image-guided navigation system, available from BrainLAB AG.

SUMMARY OF THE INVENTION

The present invention provides an improved marker system and components thereof for use with a medical navigation system, wherein the marker system includes interchangeable tracking marker holders and fastener bases for attaching the marker holders to instruments or body parts that are to be tracked during a medical procedure. In contrast to prior art adapters, the so-called reference star (herein the marker holder and tracking marker(s)) and fastener base are removably attached to one another. This enables different reference stars to be interchageably attached to a given fastener base, or vice versa, thereby to provide the best combination of reference star and fastener base for a given application. This preferably is accomplished by a standard interface between the fastener base and the holder for the tracking markers, e.g., reflective markers. In addition, surgical instruments may have integrally formed therein the standard interface, thereby eliminating the need for a fastener base. The standard interface may be configured for mounting to a fastener base or instrument in any one of multiple positions or only in a single position. In addition, the tracking markers may be removably or permanently attached to marker holder. Although the present invention is particularly applicable to marker systems employing passive reflective markers, it is also applicable to systems employing other types of markers including even active markers.

According to one aspect of the invention, there is provided a medical tracking system comprising at least one tracking marker holder and at least one fastener base. The tracking marker holder is interchangeably mountable to different fastener bases, and the fastener base is interchangeably mountable to different tracking marker holders. The fastener bases may be different sizes and/or may include different types of mechanisms for attaching the fastener base to a medical instrument or part of a patient's body. The tracking marker holders may include different characteristic arrangements of plural tracking markers, whereby each can be distinguished by the tracking system.

In a preferred embodiment, the tracking marker holder includes a marker holder body having a fastener hub at which the marker holder can be attached to the fastener base, and at least one mount for a tracking marker, which tracking marker is trackable by medical tracking equipment. The fastener hub includes a hole that opens to a mounting face of the fastener hub and which has associated therewith a fastening device. The fastening device has a coupling portion for coupling with a mating coupling of the fastener base, whereby the marker holder can be secured to the fastener base. The mounting face is provided with at least one anti-rotate element for mating with a corresponding anti-rotate element on a mounting seat of the fastener base to prevent rotation of the marker holder relative to the fastener base when the mounting face of the fastener hub is held in juxtaposition with the mounting face of the fastener base by the fastening device.

In a preferred embodiment, the fastener base includes a body having a mounting seat at which the tracking marker holder can be mounted by the fastening device associated with the tracking marker holder, and the mounting seat has at least one anti-rotate element for mating with a corresponding anti-rotate element on the mounting face of the tracking marker holder to prevent rotation of the tracking marker holder relative to the mounting seat when the mounting face of the tracking marker holder is held in juxtaposition with the mounting seat of the medical instrument by the fastening device.

The mating mounting face and mounting seat preferably function as a universal interface. In a preferred interface, the anti-rotate element of the marker holder is a recess or plural recesses in the mounting face of the adapter hub, and the anti-rotate element of the fastener base is a matching protrusion or protrusions on the mounting seat, or vice versa. The recesses and protrusions preferably are matching circular arrays of radially extending, V-shape grooves and ridges on the mounting face and seat. As will be appreciated, the fastener base or more particularly the mounting seat may be formed integrally with a medical instrument to enable direct attachment of the tracking marker holder and thereby eliminate the need for a separate fastener base.

The fastening device may have a threaded coupling portion protruding from the hole for screwing into a correspondingly threaded hole in the fastener base. The fastening device may also have at its end opposite the coupling portion a knob for rotating the fastening device.

The invention also provides a medical tracking method comprising the steps of selecting a tracking marker holder from a plurality of different tracking marker holders, selecting a fastener base from a plurality of different fastener bases, and then using the selected fastener base to attach the selected tracking marker holder to a medical instrument or part of a patient's body. Alternatively, a medical instrument equipped with the above mentioned interface may have a selected one of plural different tracking marker holders attached thereto. Thereafter, the medical instrument with one or more, and preferably three, tracking markers fixed thereto by the tracking marker holder, can be tracked by a medical tracking system in a well known manner.

The foregoing and other features of the invention are hereinafter more fully described and particularly pointed out in the claims, the following description and the annexed drawings setting forth in detail certain illustrative embodiments of the invention, these being indicative, however, of but a few of the various ways in which the principles of the invention may be employed.

BRIEF DESCRIPTION OF THE DRAWINGS

FIG. 1 is an exploded perspective view of a medical tracking system according to the invention, the system comprising a tracking marker holder and a fastener base.

FIG. 2 is a perspective view of another fastener base according to the invention.

FIG. 3 illustrates an exemplary medical instrument including a fastener base according to the invention.

FIG. 4 is a partial cross-sectional view of the medical tracking system according to the invention.

DESCRIPTION OF THE PREFERRED EMBODIMENTS

Referring now in detail to the drawings and initially to FIG. 1, an exemplary medical tracking system according to the present invention is indicated generally by reference numeral 10. The medical tracking system 10 comprises at least one tracking marker holder 12 and at least one fastener base 14 for attaching the marker holder to a medical instrument or a part of a patient's body so that the instrument or body part can be tracked by a medical tracking system in well known manner. A preferred medical tracking system is the VectorVision™ image-guided navigation system, available from BrainLAB AG. Reference may be had to U.S. Pat. No. 6,351,659 (which is hereby incorporated herein by reference in its entirety) for a description of such a system that uses passive reflective markers, although it will be appreciated that other types of tracking markers may be used in accordance with the invention for use with different types of medical navigation systems.

In a preferred embodiment of the invention, the tracking marker holder 12 is interchangeably mountable to different fastener bases 14, and the fastener base 14 is interchangeably mountable to different tracking marker holders 12. The fastener bases may be different sizes and/or may include different types of mechanisms for attaching the fastener base to a medical instrument or part of a patient's body, and the tracking marker holders may include different characteristic arrangements of plural tracking markers thereby to provide unique reference stars that can be distinguished by the medical tracking system. This enables different reference stars to be interchageably attached to a given fastener base, or vice versa, thereby to provide the best combination of reference star and fastener base for a given application.

The tracking marker holder 12 includes a marker holder body 18 and a fastening device 20. The body 18 has a fastener hub 22 at which the marker holder can be attached to the fastener base 14, and at least one mount 24 for a tracking marker 26, which tracking marker is trackable by medical tracking equipment. In the illustrated marker holder, there are three mounts for three passive reflective markers 26. The mounts may be posts to which the reflective markers may be removably attached. As is preferred, the posts are located at the distal ends of respective arms 28 that radiate from the fastener hub 22. The lengths and angular positions of the arms can be varied to provide marker holder bodies with respective unique characteristic arrangements of the tracking markers 26.

The fastener hub 22 includes a hole that opens to a mounting face 32 of the fastener hub and which has associated therewith the fastening device 20. The fastening device 20 has a coupling portion 34 for coupling with a mating coupling of the fastener base 14, whereby the marker holder can be secured to the fastener base. In the illustrated embodiment, the coupling portion 34 is threaded for screwing into a correspondingly threaded portion of a hole 36 in the body 38 of the fastener base 14, whereby the marker holder can be securely attached to the fastener base. As shown, the fastening device may have at its other end a knob 40 for hand turning of the fastening device. Although a bolt-type fastening device is illustrated, other types of fastening devices may be used, such as, for example, quick release devices, such as, for example, a ball-detent device that may be actuated by a push button.

When the holder body 18 is secured to the fastener base 14, the mounting face 32 on the fastener hub 22 is juxtaposed with a mounting seat 44 on the body 38 of the fastener base. The mounting face has an anti-rotate element for mating with a corresponding anti-rotate element on a mounting seat of the fastener base to prevent rotation of the marker holder relative to the fastener base when the mounting face of the fastener hub is held in juxtaposition with the mounting face of the fastener base by the fastening device. The mating mounting face and mounting seat preferably function as a universal interface that enables interchangeability of different marker holders with different fastener bases. In a preferred interface, the anti-rotate element of the fastener base is a protrusion or protrusions 48 on the mounting seat 44 of the adapter hub, and the anti-rotate element of the marker holder is a matching recess or recesses (not shown) in the mounting face 32, or vice versa. The recesses and protrusions preferably are matching circular arrays of radially extending, V-shape grooves and ridges on the mounting face and seat. The matching sets of circumferentially equally spaced-apart ridges and grooves allow the marker holder to be mounted in a number of different orientations.

As may be desired for some applications, a single fixed orientation may be effected by providing a pin, post or other key on one of the fastener base 14 and marker holder 12 and a mating hole, aperture or keyhole on the other. As illustrated in FIG. 4, the marker holder hub has an end of a pin 49 protruding from the mounting face thereof and the mounting seat of the fastener base has a corresponding hole 50 that receives the pin in only one position of the marker holder hub relative to the fastener base. That is, the pin height allows only one unique match between the mounting face 32 and the mounting seat 44. As can also be seen in FIG. 4, the marker holder may include an insert 51 which prevents the fastening device from separating from the marker holder hub when the marker holder is not assembled to a base or instrument.

The fastener base 14 may be provided with different types of devices for fixedly securing the fastener base to a medical instrument, such as a surgical instrument, or to a part of the patient's anatomy, such as the spine. The illustrated fastener base 14 includes a pair of clamping jaws 52 and 54 that are pivotally mounted to the body 38. The jaws are pivoted towards and away from one another by a worm screw 56 that has a knob 58 of hand rotation.

In FIG. 2, another fastener base is illustrated at 60. Like the fastener base 14, the fastener base 60 has a universal mounting seat 44 with the circular array of ridges 48 in the same identical pattern. The fastener base body 62 also has an identical opening 36 with a threaded portion into which the threaded coupling portion of the marker holder can be screwed. The fastener base 60, however, has a different clamp mechanism. The clamp mechanism includes a stationary jaw or anvil 62 and a linearly movable jaw 64. The jaw 64 is formed by a screw threaded into the body 62 and having a hand knob 66.

As above indicated, the fastener base or more particularly the mounting seat may be formed integrally with a medical instrument to enable direct attachment of the tracking marker holder and thereby eliminate the need for a separate fastener base. In FIG. 3, an exemplary medical instrument 70 (e.g., surgical forceps) can be seen to include as an integral part thereof a fastener base 72. The fastener base 72 is formed by part of the instrument body 74 and has the universal mounting seat 44 with the circular array of ridges 48.

In practice, the medical practitioner may select a tracking marker holder from a plurality of different tracking marker holders, as may be desired for mounting to a particular instrument or body part. If the instrument already has the universal interface, the tracking marker holder can be mounted directly to the instrument. Otherwise, the marker holder is mounted to a fastener base that may be selected from a plurality of different fastener bases, such a fastener base having a particular fastening modality and/or size. Then, with tracking markers fixed thereto by the marker holder, the medical instrument can be tracked by a medical tracking system in a well known manner.

Although the invention has been shown and described with respect to a certain preferred embodiment or embodiments, it is obvious that equivalent alterations and modifications will occur to others skilled in the art upon the reading and understanding of this specification and the annexed drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary embodiment or embodiments of the invention. In addition, while a particular feature of the invention may have been described above with respect to only one or more of several illustrated embodiments, such feature may be combined with one or more other features of the other embodiments, as may be desired and advantageous for any given or particular application.

What is claimed is:

1. A medical tracking system comprising at least one tracking marker holder and at least one fastener base, the tracking marker holder being interchangeably mountable to different fastener bases, and the fastener base being interchangeably mountable to different tracking marker holders, wherein the tracking marker holder includes a marker holder body having a fastener hub at which the marker holder can be attached to the fastener base, and a plurality of mounts for mounting respective tracking markers in a fixed positional relationship to the fastener hub, which tracking markers are trackable by medical tracking equipment, the fastener hub including a hole that opens to a mounting face of the fastener hub; and a fastening device associated with the hole and having a coupling portion for coupling with a mating coupling of the fastener base, whereby the marker holder can be secured to the fastener base, and wherein the mounting face is provided with at least one anti-rotate element for mating with a corresponding anti-rotate element on a mounting seat of the fastener base to prevent rotation of the marker holder relative to the fastener base when the mounting face of the fastener hub is held in juxtaposition with the mounting seat of the fastener base by the fastening device.

2. The tracking system of claim 1, wherein the at least one fastener base includes a plurality of fastener bases of different sizes.

3. The tracking system of claim 1, wherein the at least one fastener base includes a plurality of fastener bases including respective different types of mechanisms for attaching the fastener base to a medical instrument or part of a patient's body.

4. The tracking system of claim 3, wherein the fastener bases have different clamping mechanisms for attachment to different instruments or parts of a patient's body.

5. The tracking system of claim 1, wherein the at least one tracking marker holder includes a plurality of tracking marker holders having respective different characteristic arrangements of plural tracking markers.

6. The tracking system of claim 1, wherein the fastener base includes a body having a mounting seat at which the tracking marker holder can be mounted by the fastening device associated with the tracking marker holder, and the mounting seat has at least one anti-rotate element for mating with a corresponding anti-rotate element on the mounting face of the fastener hub to prevent rotation of the tracking marker holder relative to the mounting seat when the mounting face of the fastener hub is held in juxtaposition with the mounting seat of the medical instrument by the fastening device.

7. The tracking system of claim 1, wherein the at least one mount includes posts to which reflective balls can be removably attached.

8. The tracking system of claim 7, wherein the marker holder includes a plurality of arms extending from the fastener hub, and the posts are located at distal ends of the arms.

9. The tracking system of claim 1, wherein the fastening device has a threaded coupling portion protruding from the hole.

10. The tracking system of claim 9, wherein the fastening device has at its end opposite the coupling portion a knob for rotating the fastening device.

11. The tracking system of claim 1, comprising a medical instrument including the fastener base.

12. The tracking system of claim 1, wherein the fastener base includes a body and at least one movable clamping jaw, the body having a mounting seat at which the tracking marker holder can be mounted by the fastening device, and the mounting seat having at least one anti-rotate element for mating with the corresponding anti-rotate element on the mounting face of the tracking marker holder to prevent rotation of the tracking marker holder relative to the mounting seat when the mounting face of the tracking marker holder is held in juxtaposition with the mounting seat by the fastening device.

13. A medical tracking system according to claim 1, further comprising the tracking markers.

14. A medical tracking system according to claim 13, wherein the tracking markers are passive reflective markers.

15. A medical tracking system comprising at least one tracking marker holder and at least one fastener base, the tracking marker holder being interchangeably mountable to different fastener bases, and the fastener base being interchangeably mountable to different tracking marker holders, wherein the tracking marker holder includes a plurality of mounts for mounting respective tracking markers in a fixed positional relationship to a fastener hub of the tracking marker holder, which tracking markers are trackable by medical tracking equipment, and wherein the fastener base includes a body having a mounting seat at which the tracking marker holder can be mounted by a fastening device associated with the tracking marker holder, and the mounting seat has at least one anti-rotate element for mating with a corresponding anti-rotate element on a mounting face of the tracking marker holder to prevent rotation of the tracking marker holder relative to the mounting seat when the mounting face of the tracking marker holder is held in juxtaposition with the mounting seat of the body by the fastening device.

16. The tracking system of claim 15, wherein the anti-rotate element is a recess in the mounting face of the fastener hub.

17. The tracking system of claim 16 wherein the recess extends radially with respect to a hole in the tracking marker holder.

18. The tracking system of claim 15, wherein the at least one anti-rotate element includes a plurality of circumferentially equally spaced-apart grooves, and the grooves extend radially with respect to a hole in the tracking marker holder.

19. The tracking system of claim 15, wherein the at least one anti-rotate element includes a circular array of circumferentially spaced-apart grooves, and the fastening device is held within a hole in the tracking marker holder for rotation about an axis that is coaxial with a center axis of the circular array.

20. The tracking system of claim 15, wherein the anti-rotate element is a groove and the groove has converging side walls.

21. The tracking system of claim 20, wherein the groove is V-shape in cross-section.

22. The tracking system of claim 15, wherein the anti-rotate element is a protrusion on the mounting seat.

23. The tracking system of claim 22, wherein the protrusion is a ridge that extends radially with respect to a hole in the body that opens to the mounting seat.

24. The tracking system of claim 15, wherein the at least one anti-rotate element includes a plurality of circumferentially equally spaced-apart ridges, and the ridges extend radially with respect to the hole that opens to the mounting seat.

25. The tracking system of claim 15, wherein the at least one anti-rotate element includes a circular array of circumferentially spaced-apart ridges, and the hole that opens to the mounting seat has an axis that is coaxial with a center axis of the circular array.

26. The tracking system of claim 15, wherein the anti-rotate element is a ridge and the ridge has converging side walls.

27. The tracking system of claim 15, wherein the ridge is V-shape in cross-section.

28. The tracking system of claim 15, wherein a hole in the body has a threaded portion for threaded receipt of a threaded coupling portion of the fastening device.

29. A medical tracking system according to claim 15, further comprising the tracking markers.

30. A medical tracking system according to claim 29, wherein the tracking markers are passive reflective markers.

31. A medical tracking system comprising at least one tracking marker holder and at least one fastener base, the tracking marker holder being mountable to a fastener base, and the fastener base being mountable to a tracking marker holder, wherein the tracking marker holder includes a marker holder body having a fastener hub at which the marker holder can be attached to the fastener base, and a plurality of mounts for mounting respective tracking markers in a fixed positional relationship to the fastener hub, which tracking markers are trackable by medical tracking equipment, the fastener hub including a hole that opens to a mounting face of the fastener hub; and a fastening device associated with the hole and having a coupling portion for coupling with a mating coupling of the fastener base, whereby the marker holder can be secured to the fastener base, and wherein the mounting face is provided with at least one anti-rotate element for mating with a corresponding anti-rotate element on a mounting seat of the fastener base to prevent rotation of the marker holder relative to the fastener base when the mounting face of the fastener hub is held in juxtaposition with the mounting face of the fastener base by the fastening device.

* * * * *